US009155465B2

(12) United States Patent
Abramoff et al.

(10) Patent No.: US 9,155,465 B2
(45) Date of Patent: Oct. 13, 2015

(54) SNAPSHOT SPECTRAL DOMAIN OPTICAL COHERENCE TOMOGRAPHER

(71) Applicant: IDx, LLC, Iowa City, IA (US)

(72) Inventors: Michael D. Abramoff, University Heights, IA (US); Edward DeHoog, Long Beach, CA (US)

(73) Assignee: IDX, LLC, Iowa City, IA (US)

( * ) Notice: Subject to any disclaimer, the term of this patent is extended or adjusted under 35 U.S.C. 154(b) by 0 days.

(21) Appl. No.: 14/266,263

(22) Filed: Apr. 30, 2014

(65) Prior Publication Data
US 2014/0320816 A1  Oct. 30, 2014

Related U.S. Application Data

(60) Provisional application No. 61/817,413, filed on Apr. 30, 2013.

(51) Int. Cl.
*A61B 3/10* (2006.01)
*G01B 9/02* (2006.01)
*G01J 3/45* (2006.01)

(52) U.S. Cl.
CPC .......... *A61B 3/102* (2013.01); *G01B 9/02027* (2013.01); *G01B 9/02028* (2013.01); *G01B 9/02044* (2013.01); *G01B 9/02091* (2013.01); *G01J 3/45* (2013.01); *G01B 2290/65* (2013.01)

(58) Field of Classification Search
CPC ............ A61B 3/102; A61B 3/14; A61B 3/12; A61B 3/10; A61B 3/1225
USPC ................... 351/206, 246, 205; 356/326, 328
See application file for complete search history.

(56) References Cited

U.S. PATENT DOCUMENTS

2007/0015969 A1   1/2007   Feldman et al.
2007/0258095 A1   11/2007  Olivier et al.
2008/0117424 A1   5/2008   Teramura et al.
(Continued)

FOREIGN PATENT DOCUMENTS

EP        0943075 B1     6/2005
WO    2012078471 A1     6/2012

OTHER PUBLICATIONS

Abramoff et al., "Image Processing", Chapter 6, Publisher: Ryan.
(Continued)

*Primary Examiner* — Hung Dang
(74) *Attorney, Agent, or Firm* — Davis Brown Law Firm; Matthew Coryell

(57) ABSTRACT

Provided is a snapshot spectral domain optical coherence tomographer comprising: a light source providing a plurality of beamlets; a beam splitter, splitting the plurality of beamlets into a reference arm and a sample arm; a first optical system that projects the sample arm onto multiple locations of a sample; a second optical system for collection of a plurality of reflected sample beamlets; a third optical system projecting the reference arm to a reflecting surface and receiving a plurality of reflected reference beamlets; a parallel interferometer that provides a plurality of interferograms from each of the plurality of sample beamlets with each of the plurality of reference beamlets; an optical image mapper configured to spatially separate the plurality of interferograms; a spectrometer configured to disperse each of the interferograms into its respective spectral components and project each interferogram in parallel; and a photodetector providing photon quantification.

20 Claims, 13 Drawing Sheets

(56) References Cited

U.S. PATENT DOCUMENTS

| | | |
|---|---|---|
| 2009/0225277 A1* | 9/2009 | Gil .............................. 351/206 |
| 2009/0268161 A1 | 10/2009 | Hart et al. |
| 2011/0176138 A1 | 7/2011 | Khalil et al. |
| 2011/0220798 A1 | 9/2011 | Baurichter et al. |
| 2011/0299034 A1 | 12/2011 | Walsh et al. |
| 2012/0176625 A1 | 7/2012 | Huntley et al. |
| 2012/0307258 A1 | 12/2012 | Koerner et al. |
| 2014/0218684 A1* | 8/2014 | Kumar et al. ................ 351/206 |

OTHER PUBLICATIONS

Yaqoob et al., "Spectral domain optical coherence tomography: a better OCT imagin strategy", "Molecular Imaging", Dec. 1, 2005, pp. 8-13.

* cited by examiner

SNAPSHOT SPECTRAL DOMAIN OPTICAL COHERENCE TOMOGRAPHER

CROSS-REFERENCE TO RELATED APPLICATION(S)

This application claims priority from U.S. Provisional Application No. 61/817,413, filed Apr. 30, 2013, which is hereby incorporated herein by reference in its entirety.

FIELD OF THE INVENTION

The present invention relates to optical coherence tomography imagers.

BACKGROUND OF THE INVENTION

Optical Coherence Tomography (OCT) is a technique to measure depth dependent refractive index changes at a single location, and can be used for two- and three-dimensional imaging of tissue and other semi-transparent materials. 3D OCT is primarily used in the eye, to image the retina and retinal abnormalities and the cornea and corneal abnormalities at high resolution. The principle of OCT is based upon low-coherence interferometry, where the backscatter from more outer retinal tissues can be differentiated from that of more inner tissues because it takes longer for the light to reach the sensor. Because the differences between the most superficial and the deepest layers in the retina and the cornea are around 100-400 µm, the difference in time of arrival is very small and requires interferometry to measure. The spectral-domain OCT (SDOCT) improvement of the traditional time-domain OCT (TDOCT) technique, known also as Fourier domain OCT (FDOCT), makes this technology suitable for real-time cross-sectional retinal imaging at video rate.

OCT imagers presently on the market are expensive and complex because they depend on scanning across the retina, which is typically performed through galvanic mirrors that deflect measurement light. Galvanic minors require precise adjustment, have finite latency and response time, and substantially increase complexity and cost of OCT imagers. Because of this substantial cost and complexity, the availability of OCT imagers is limited and thus many in the population have limited access to retinal examinations that could be key to the early detection and preventative treatment of conditions such as diabetic retinopathy. There is a need in the art for a low-cost OCT imager that could be cheaply and easily deployed to locations such as primary care clinics, drug stores and retail stores, or even at home to allow for increased access to high quality retinal scans.

BRIEF SUMMARY OF THE INVENTION

In an aspect, provided is a snapshot spectral domain optical coherence tomographer comprising a light source providing a plurality of beamlets; a beam splitter, splitting the plurality of beamlets into a reference arm and a sample arm; a first optical system that projects the sample arm onto multiple locations of a sample; a second optical system for collection of a plurality of reflected sample beamlets; a third optical system projecting the reference arm to a reflecting surface and receiving a plurality of reflected reference beamlets; a parallel interferometer that provides a plurality of interferograms from each of the plurality of sample beamlets with each of the plurality of reference beamlets; an optical image mapper configured to spatially separate the plurality of interferograms; a spectrometer configured to disperse each of the interferograms into its respective spectral components and project the spectral components of each interferogram in parallel; and a photodetector configured to receive the spectral components of each interferogram and provide in parallel photon quantification.

In an aspect, provided is a snapshot spectral domain optical coherence tomographer comprising a housing and a system of optical components disposed in the housing capable of parallel optical coherence imaging of a sample; a broadband low coherence light source providing light to a beam splitter wherein the beam splitter splits the light into a reference arm and a sample arm; a first optical element converting the sample arm into a plurality of beamlets and focusing the plurality of beamlets on the sample; a reflecting surface reflecting light from the reference arm, wherein the light reflected from the reflecting surface is recombined with the plurality of beamlets reflected from the sample producing a plurality of beamlet interferograms; an optical image mapper configured to receive and spatially separate the plurality of beamlet interferograms; a spectrometer configured to disperse each of the beamlet interferograms into its respective spectral components and project the spectral components of each interferogram in parallel; a photodetector configured to receive the spectral components of each beamlet interferogram and provide in parallel photon quantification; and a computer module wherein said computer module performs inverse transforms on the photon quantifications and quantifies intensities at each depth.

In an aspects, provided is method of imaging an eye comprising providing a plurality of low coherence beamlets; transmitting the plurality of low coherence beamlets to a beam splitter, wherein the beam splitter splits the plurality of beamlets into a reference arm directed to a reflecting surface and a sample arm directed to multiple locations of an eye; recombining beamlets reflected from the reflecting surface and beamlets reflected from the eye generating a plurality of interferograms; converting the plurality of beamlets to a linear array of beamlets; dispersing each of the plurality of beamlets into its spectral components; and performing in parallel photon quantification of each of the plurality of beamlets.

In an aspect, the method further comprises performing inverse transforms on the photon quantifications and quantifying the intensities at each depth of the eye. In certain aspects, the method further comprises interpreting the intensities and providing an aggregate response of the eye. In still further aspects, the method further comprises calculating retinal thickening. In yet further aspects, the method further comprises calculating nerve fiber layer thinning.

DETAILED DESCRIPTION

Figure 1:
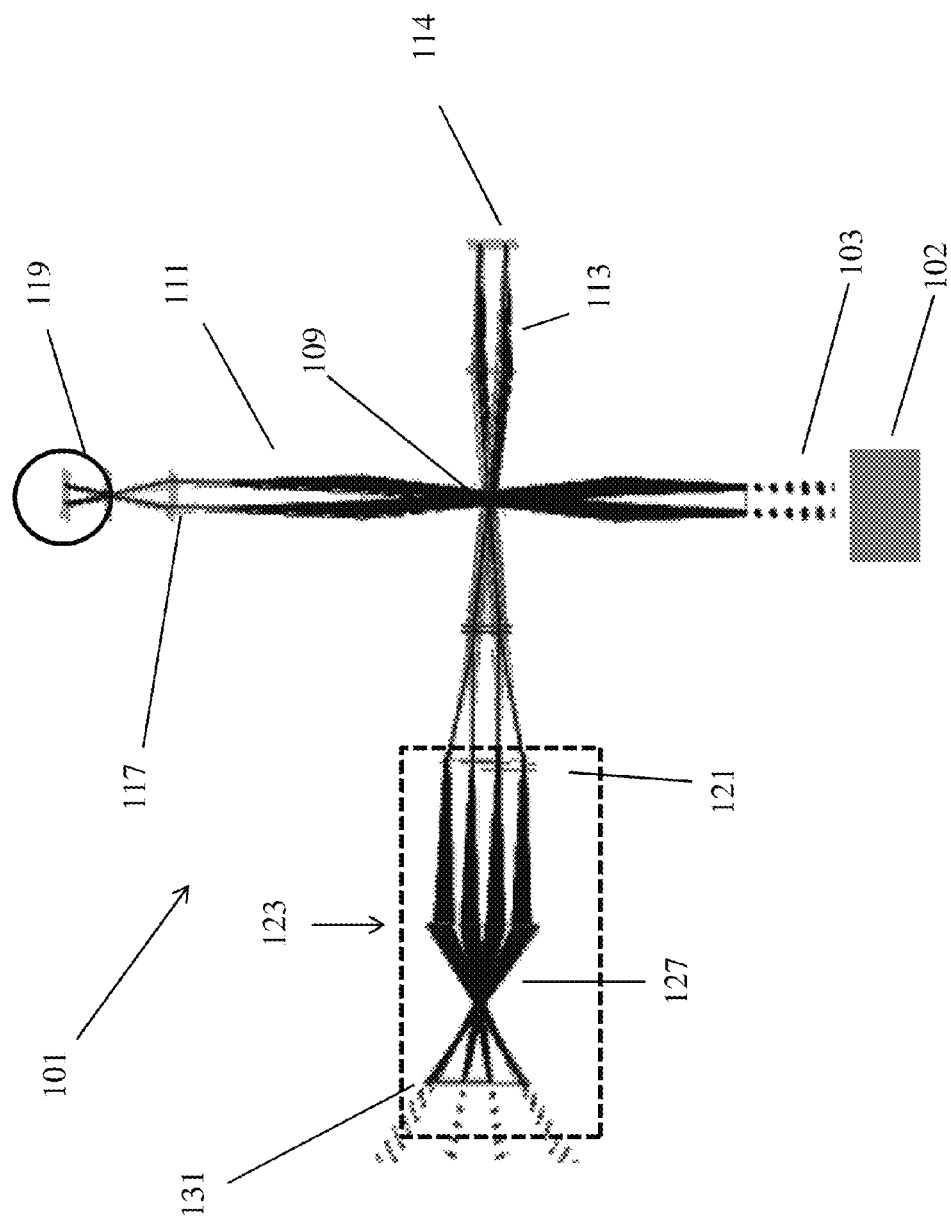
FIG. 1 is a schematic diagram of the snapshot OCT apparatus according to certain embodiments.

The invention now will be described more fully with reference to the accompanying drawings, in which illustrative embodiments of the invention are shown. Although the present invention has been described with reference to preferred embodiments, persons skilled in the art will recognize that changes may be made in form and detail without departing from the spirit and scope of the invention.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

In exemplary embodiments, the apparatus disclosed herein is a snapshot spectral domain optical coherence tomographer comprising a housing and a system of optical components disposed in the housing capable of parallel optical coherence imaging of an object. An array of broadband low-coherence light sources provides a plurality of beamlets and a beam splitter positioned to receive the plurality of beamlets splits the plurality of beamlets into a reference arm and a sample arm, with each arm comprising a plurality of beamlets. A first optical system projects the sample arm onto multiple locations of a sample to create a sparse sampling of the object. A second optical system collects the plurality of beamlets reflected from the sample and a third optical system projects the reference arm onto a reflecting surface and collects a plurality of reflected beamlets. The reflected light from the sample arm and reference arms are recombined create optical interference an projected to an optical image mapper. The optical image mapper is configured to spatially separate the beamlets. A spectrometer disperses each of the interferograms into its respective spectral components and projects the spectral components of each interferogram in parallel to a focal plane photodetector. The photodetector provides parallel quantification of the photons from the spectral components of each the interferograms.

A computer module performs inverse transforms on said photon quantifications and quantifies the intensities at each sample depth. A second computer module interprets the intensities and provides an aggregate response of the sample which can then be output as a visual display.

In certain alternative embodiments, a light source or multiple light sources are directed into an interferometric system where light is split and recombined to form interference fringes. Incident light is divided into a sample and reference path by use of a beam splitter. Light from the source or sources pass through a beam splitter and is split into reference and sample arms. Light in the sample arm is converted into beamlets which are focused on the sample. Beamlets are reflected by the sample and return along the same path of incidence. As light from the sample arm passes through the beam splitter it is directed to an image mapper. Light in the reference arm is reflected by a minor and directed toward the image mapper. Light from the reference and sample are recombined in the path containing the image mapper in order to form optical interference. The image mapper receives the recombined light from the sample arm and reference arm as a rectilinear grid and converts the rectilinear grid into a linear array allowing for the spectrum of each beamlet to be sampled in a direction substantially perpendicular to the dimension of the linear array.

According to certain embodiments, the apparatus can be configured to image various sample tissues. In certain implementation, the snapshot apparatus is configured to image the retina. In further implementations, the apparatus is configured to image the cornea. In still further implementations, the apparatus is configured to image ocular epithelium, nervous tissue, or endothelium. One skilled in the art will appreciate that the apparatus can be configured for imaging other tissue types.

Turning now to the figures, FIG. 1 shows a schematic diagram of the geometry of the apparatus 101 according to certain embodiments. An array of broadband low-coherence light sources 102 provide a plurality of beamlets 103. The broadband low-coherence light source can be light emitting diodes (LEDs), superluminescent diodes (SLD), or Ti:Saph laser. Other light sources are possible. In certain exemplary implementations, an array of point sources is created by using multiple light sources arranged in a grid. In certain alternative embodiments, a single light source can be converted into multiple point sources by the use of a lenslet array, multifaceted reflector, or other optics capable of converting a single source into multiple point sources. According to certain implementations, gradient-index optics are used. These multiple sources enable/create multiple beamlets for sparse sampling of the sample.

Prior art scanning OCT systems have typically sampled using grids of approximately 100×500 μm generating thousands of samples over an area of, for example, 6×6 mm. In contrast, according to certain embodiments, a single snapshot may comprise only hundreds of individual point samples over a grid of, for example 2000×2000 μm over a larger area of sample, for example 10×10 mm. One skilled in the art will appreciate that a range sparse sampling grids are possible.

The beamlets are projected to a beam splitter 109 which splits the beams into a reference arm 113 and a sample arm 111, with each arm comprising of a plurality of beamlets. The sample arm 111 is projected to a sample objective 117 which projects the sample arm 111, in focus and in phase, onto multiple locations of a sample to be imaged 119. Because the beamlets cover a wide area of the sample in a single "snapshot", the need to scan the sample along the XY plane is eliminated as are the galvanic mirrors and other moving parts that are required for such scanning. The size of the beamlet array can be adjusted to cover any desired field by changing the collimation/relay or projection optics responsible for delivering the beamlets to the sample. Sampling density can be changed by increasing the number of sources or increasing the number of facets, lenslets, or other structures responsible for generating multiple beamlets.

According to certain alternative embodiments, the disclosed apparatus is a hybrid of conventional scanning OCT and snapshot OCT. According to these embodiments, multiple snapshots (each with sparse sampling of the sample) are taken sequentially. The sequential snapshots are integrated to yield an image with greater spatial field of view or increasing the sampling density. This has the effect of yielding an image spatial resolution similar to that of a scanning OCT system but at reduced cost and complexity of the galvanic scanning minors.

Light reflected from the multiple locations on the sample 119 is collected into parallel beamlets by an objective 117 and projected back to the beam splitter 109. Light from the reference arm 113 is reflected from the reference minor 114 and back to the beam splitter where it is recombined with light reflected by the sample 119 to generate a plurality of interferograms from the interference between the sample arm beamlets and the reference arm beamlets. The plurality of interferograms are projected onto an image mapper system 121. Light enters the image mapper system 121 as a square array which the image mapper system 121 converts into a linear array and projects on to a spectrometer 123. Within the spectrometer 123, the interferograms are dispersed into their spectral components 127. The spectral components of each of the interferograms are detected along the focal plane array 131. The focal plane array 131 detects and quantifies the photons of each interferogram in parallel, thus preserving the spatial relationship from the sample 119.

Figure 2A:
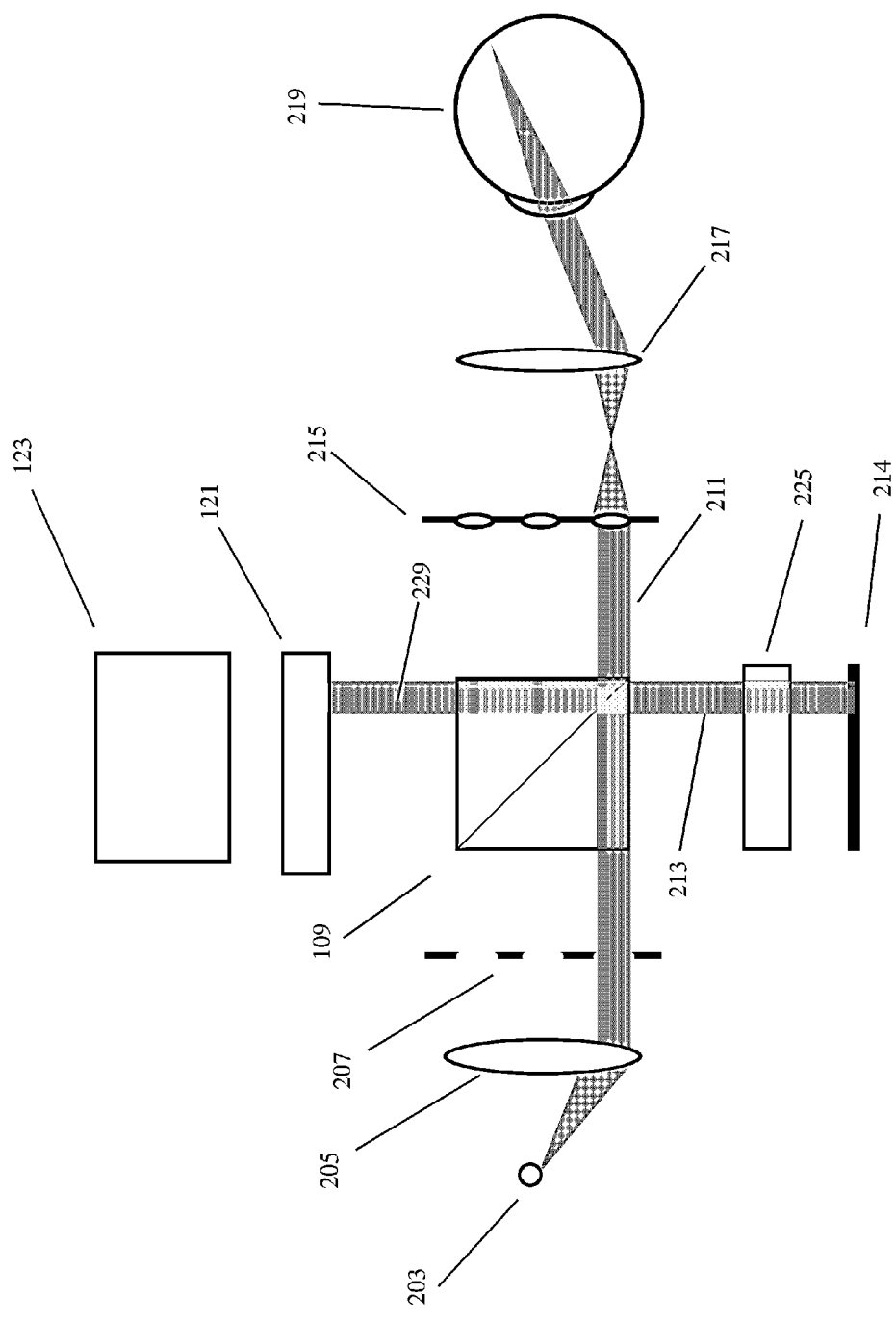
FIGS. 2A-B are schematic diagrams of alternative embodiments of the snapshot OCT apparatus, according to certain embodiments.

FIG. 2A shows a schematic diagram of an alternative embodiment wherein rather than providing beamlets from an array of low-coherence light sources, a single low coherence light source is used and beamlets are produced after the beam has been split. According to these embodiments, a broadband low-coherence light source 203 projects low-coherence light to a beam splitter 109 that splits the beam into a sample arm 211 and a reference arm 213. According to certain embodiments, the light from the low coherence light source 203 is first project through a first objective 205 and an aperture array 207 before being projected to the beam splitter 109.

In certain embodiments, the sample beam 211 is then split by a lenslet array 215 into a plurality of sample beamlets that are projected through an objective 217 onto the sample to be imaged 119. Other means of generating sample beamlets are possible. The sample beamlets are projected onto the multiple locations within the sample 119, in focus and in phase. The beamlets are reflected by the sample 119 and collected in parallel by the objective 217. A reference objective projects the reference arm 213 to a reference minor 214 and collects the reflected beam. According to certain embodiments, light reflected from the reference mirror 214 is projected to a dispersion compensation element 225. Light reflected from the sample 219 and the reference mirror 214 are recombined at the beam splitter 109 to produce a plurality of interferograms which are projected to an image mapper system 121 as a square array. The image mapper system 121 coverts the square array into a linear array and spatially separates the plurality of interferograms. The plurality of interferograms are then projected to a spectrometer 123 which disperses each interferogram into each of its spectral components and projects the spectral components onto a photo-detector (not shown).

Figure 2B:
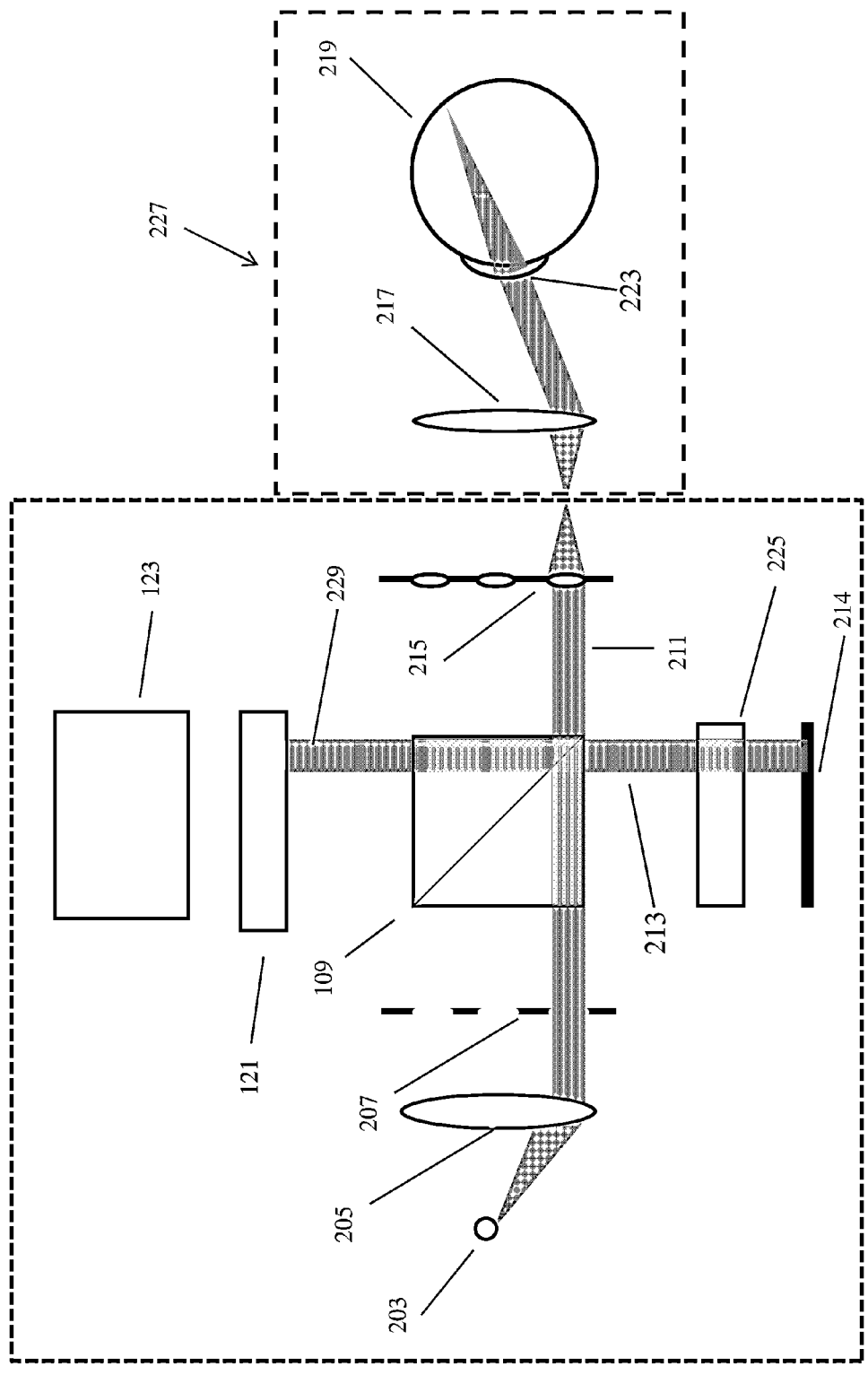

In an alternative embodiment, best shown in FIG. 2B, the snapshot apparatus is integrated with a fundus camera 227 for imaging the retinal tissues. The parallel OCT device creates an array of sampling points and the fundus integration system projects the array of sampling points onto the ocular tissues to achieve sparse sampling of the eye 219. In certain implementations, sparse sampling of the eye is achieved by use of an objective lens 217 where the beamlets used for sampling the retina are placed at the front focus of the objective 217. The eye 219 is located at the back focus of the objective such that the beamlets are collimated and directed thru the pupil 223 of the eye 219. The optics of the eye focus the beamlets on the retina at multiple field points. The multiple sampled beamlets are reflected or scattered by the retina back along the original path of incidence. Beamlets used to sample the retina are then recombined with the light reflected from the reference minor 214 to form interference fringes 229 which are projected to the image mapper 121.

Figure 3:
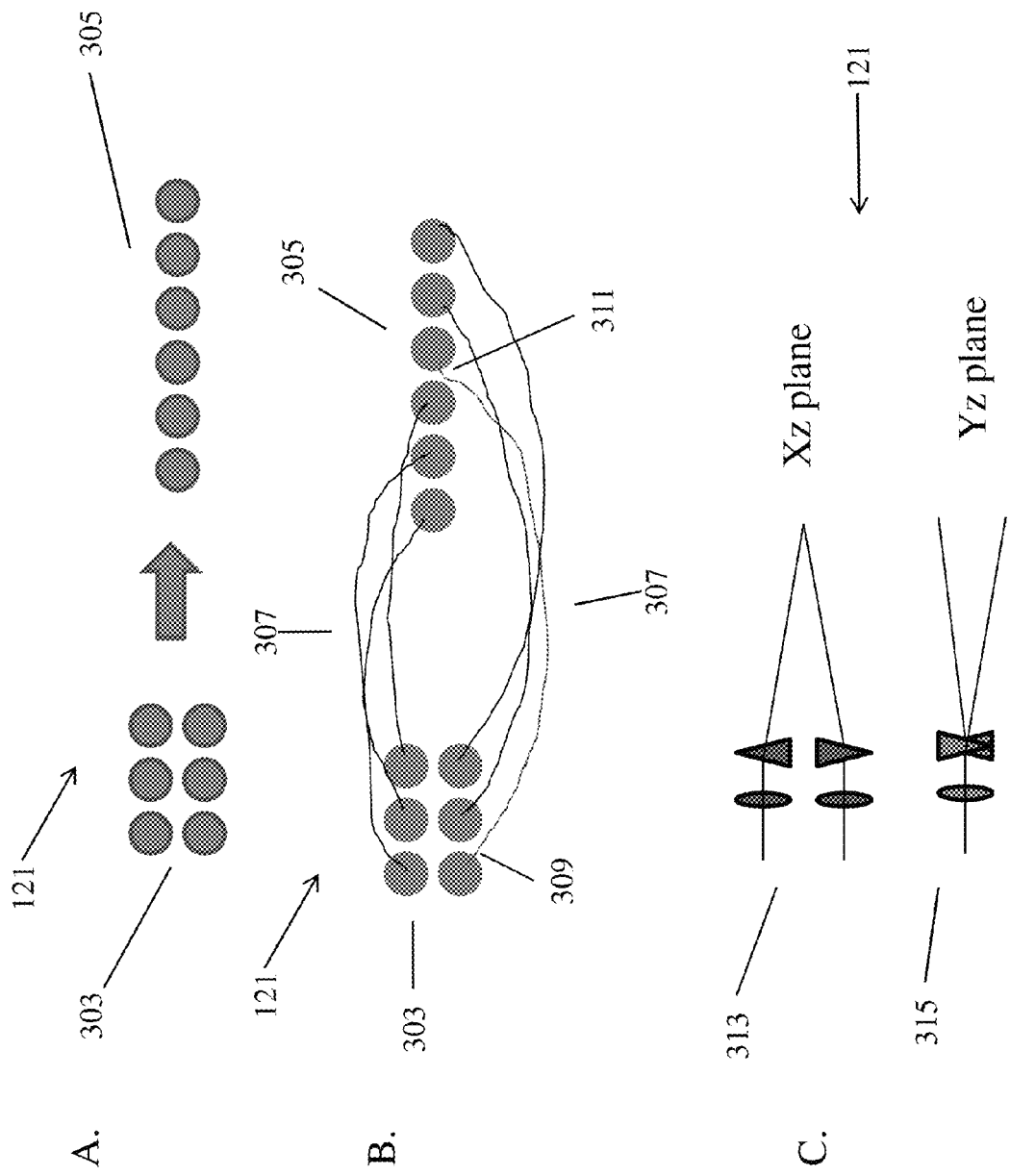
FIGS. 3A-C are diagrams of image mapper optical configurations, according to certain embodiments.

FIG. 3A shows a schematic diagram of the image mapper system 121 according to certain embodiments. The image mapper system 121 spatially separates the beamlets from the reference and sample arm according to their point of reflection from the reference minor and sample respectively. The light entering image mapper system 121 enters as a square or rectilinear array 303 and must be converted to a linear array 305. One skilled in the art will appreciate that multiple approaches can be used to affect this conversion. According to certain embodiments, best shown in FIG. 3B, the square array 303 is converted to a linear array 305 using fiber optics 305. In such an embodiment, the image mapper system uses a plurality of optical fibers 307, with fiber each having collecting end 309 end and transmitting end 311. The collecting end 309 is positioned to receive scattered light in a non-linear array from the reference and sample arms. The transmitting ends 311 are positioned in a linear array 305 such that the transmitted light can be detected and quantified by the photodetector.

In alternative embodiments, best shown in FIG. 3C, a prism array is used. Two configurations are shown. A first configuration 313 separates spatial information in the XZ plane. A second configuration 315 separates spatial information in the YZ plane. The prism array is a multifaceted array of prisms where each prism has a specific set of tilt angles for converting a rectilinear grid of beamlets into a linear array of beams. Other configurations are possible as will be appreciated by one skilled in the art.

Figure 4:
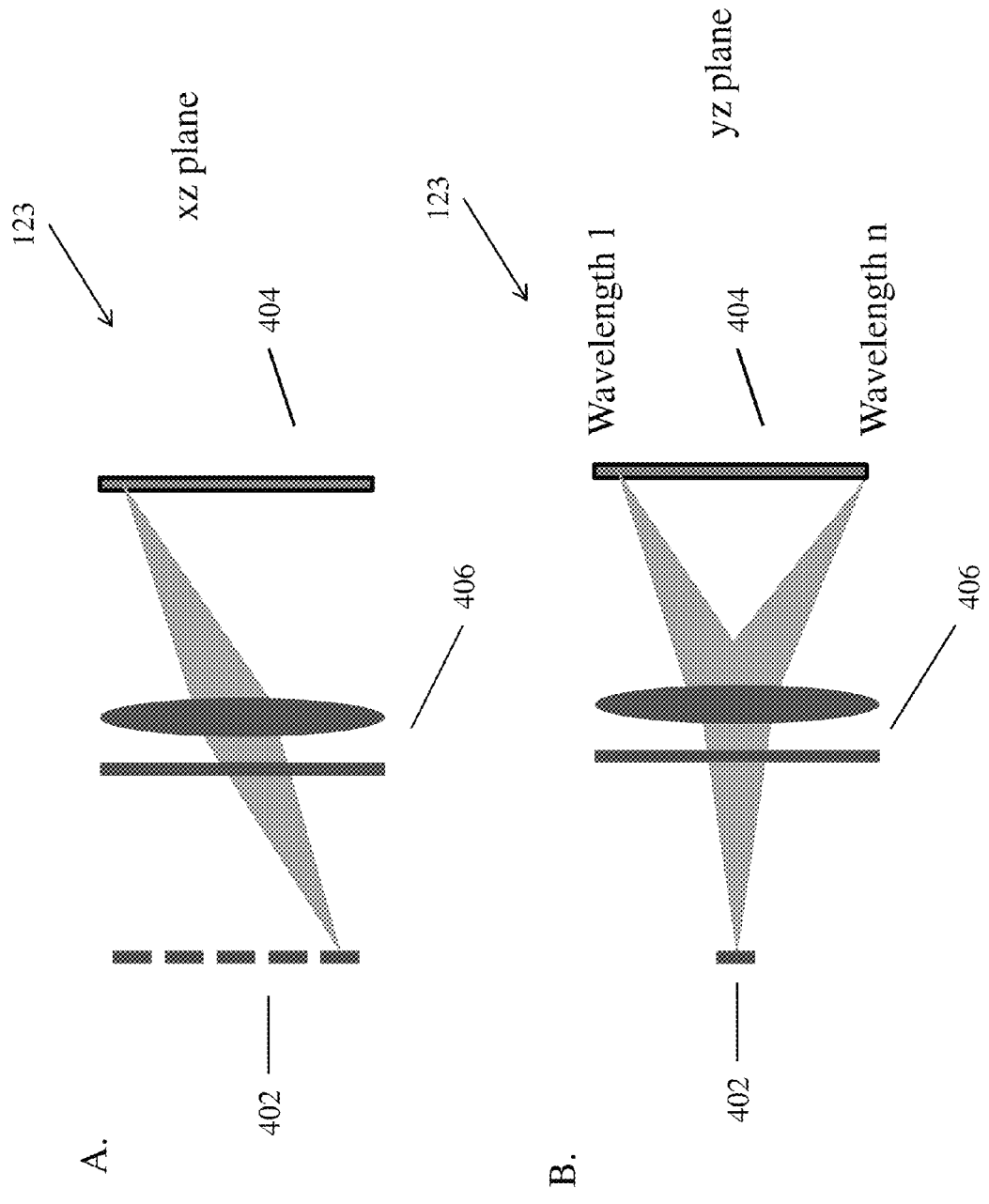
FIG. 4A-B are diagrams of the spectrometer, according to certain embodiments.

FIGS. 4A-B are schematics showing an optical spectrometer according to certain embodiments in which an array of point objects from the image mapper 402 is imaged onto a two dimensional detector array 404. A grating prism 406 or other dispersive device separates the spectral content (wavelength information) along the direction substantially perpendicular to the array of point sources 402. In FIG. 4A a linear array of points is imaged onto a CCD 404. This is shown in the xz plane. In FIG. 4B the same device is dispersing the spectrum along a direction substantially perpendicular to the input array 402. The spectral information for each point is projected in the yz plane. This arrangement allows the spectral information of each point to be gathered simultaneously on a two dimensional detector array 404 without scanning.

Figure 5:
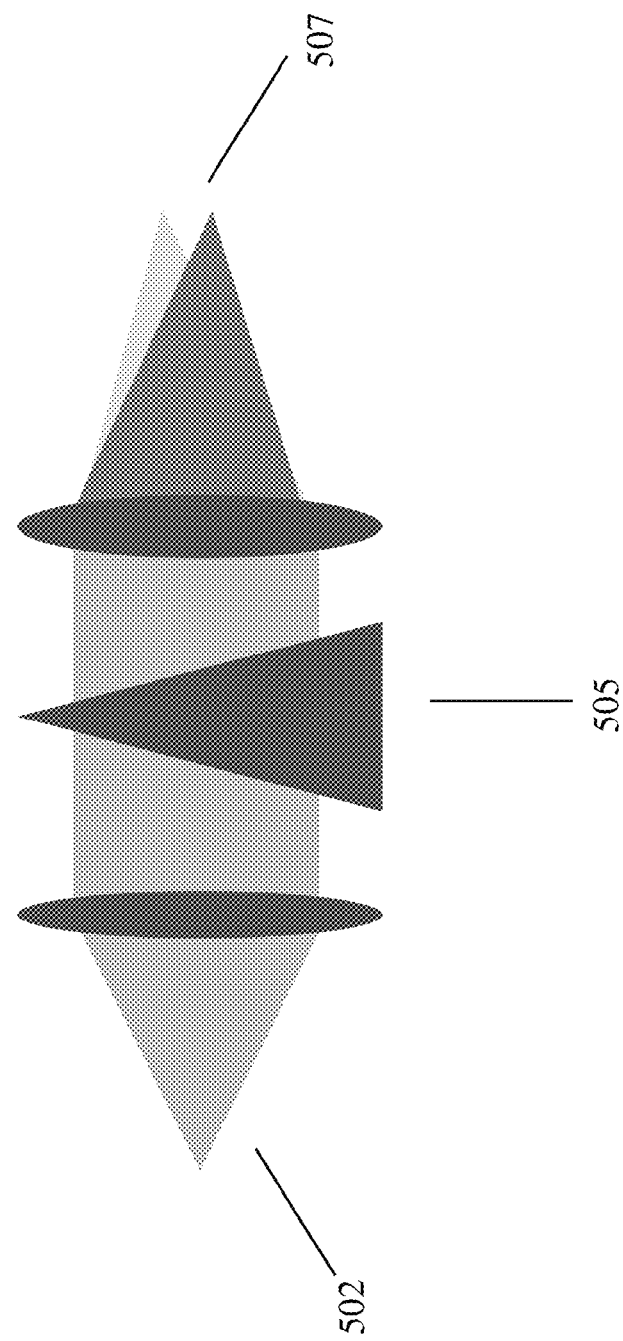
FIG. 5 is schematic diagram of the spectrometer dispersive device, according to certain embodiments.
Figure 6:
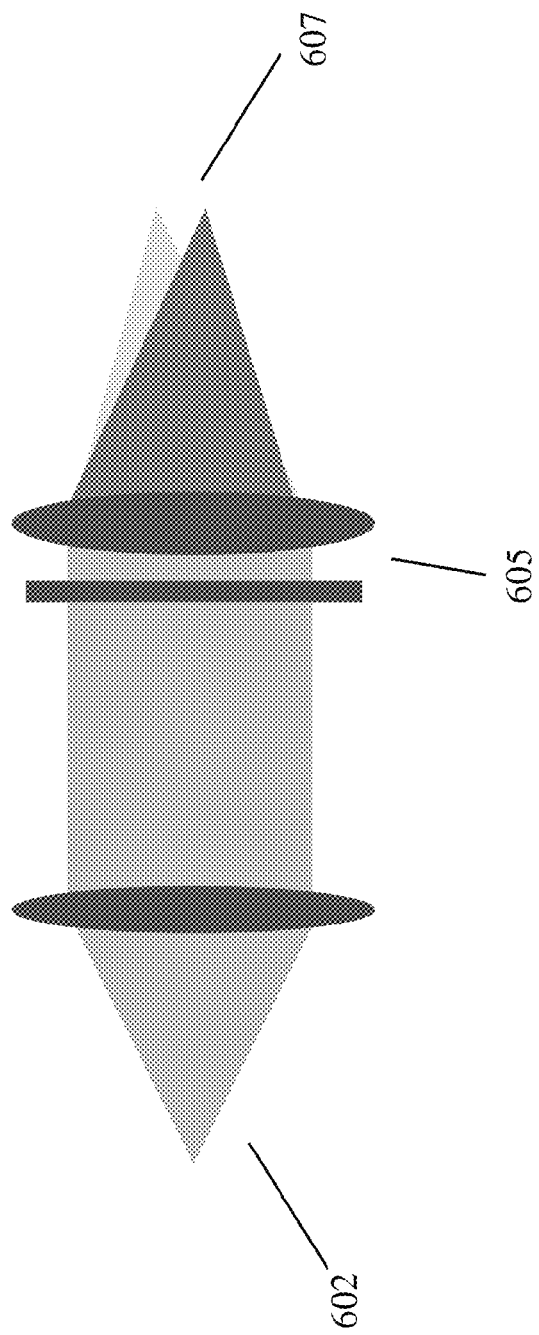
FIG. 6 is schematic diagram of the spectrometer dispersive device, according to certain embodiments.

In certain implementations, best shown in FIG. 5, the spectrometer's dispersive device is a prism 505. In this implementation, light from the image mapper 502 is projected to prism 505 and dispersed into its spectral components 507. In further implementations, best shown in FIG. 6, the spectrometer's dispersive device is a diffraction grating 605. In this implementation, light from the image mapper 602 is projected to prism 605 and dispersed into its spectral components 607. As will be appreciated by those skilled in the art, other dispersive devices are possible, such as holographic gratings.

Figure 7:
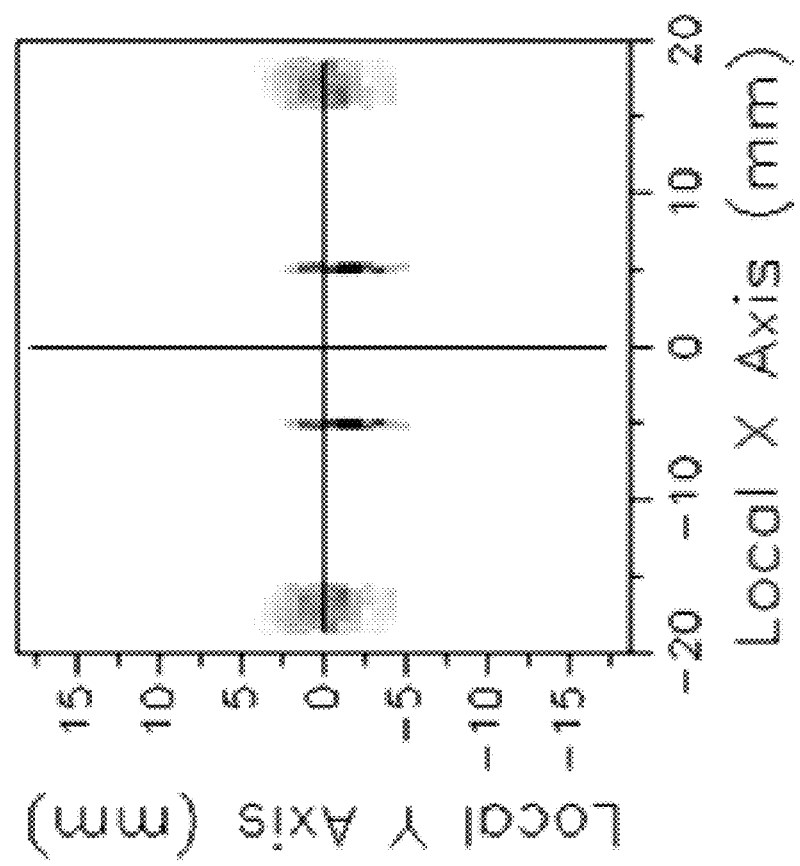
FIG. 7 is an image of the spectrum from point sources from the detector plane, according to certain embodiments.

FIG. 7 shows a representative view of data collected from the focal detector plane according to certain embodiments. Each spectrum 709 represents the interferogram from a single beamlet/point in the object. The x-axis is distance from center of the interferogram in millimeters along the X-axis. Y-axis represents wavelength information of the spectrum and encodes depth in the sample.

Figure 8:
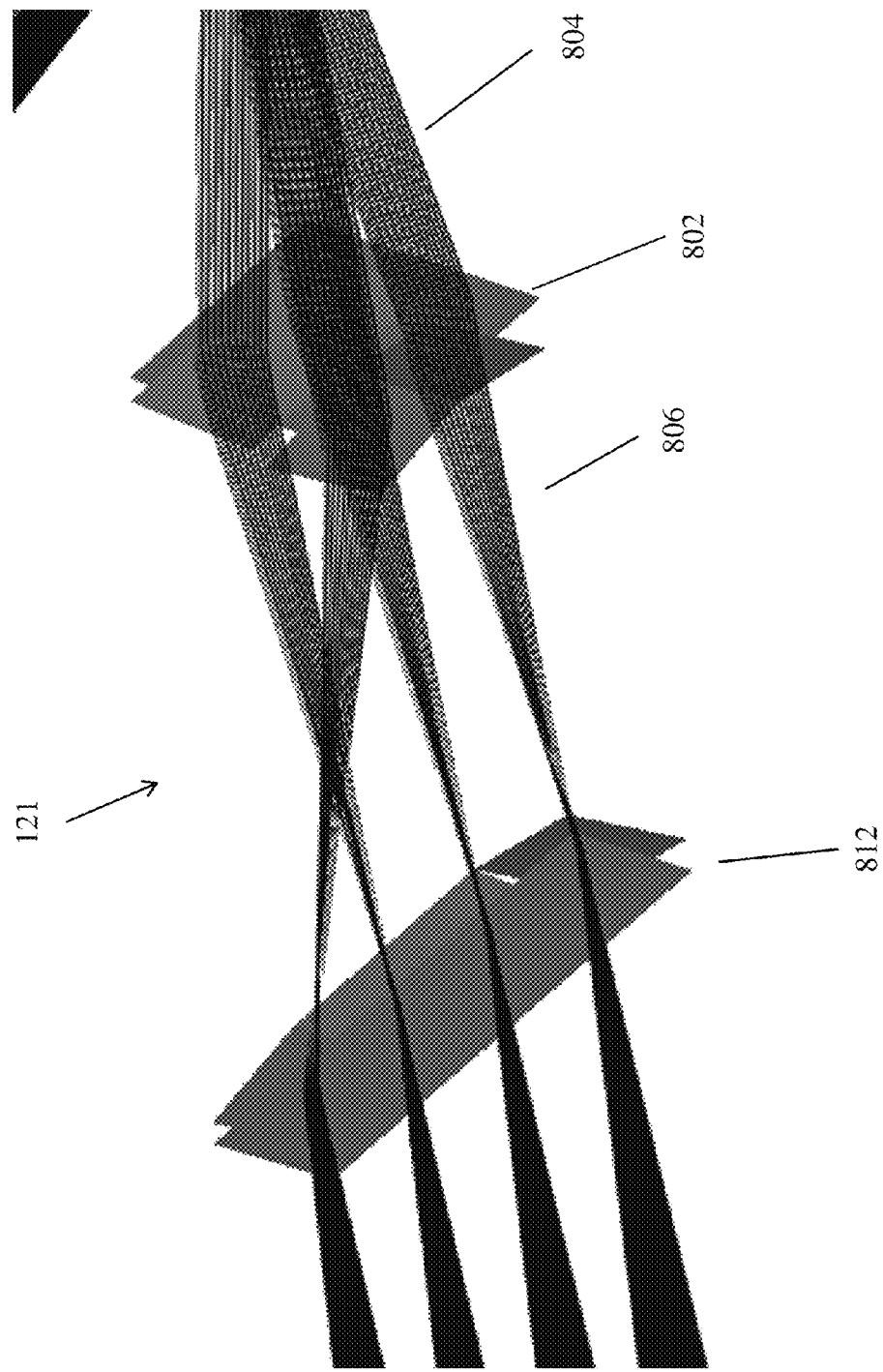
FIG. 8 is a diagram of the image mapper optics, according to certain embodiments.

FIG. 8 is a schematic model of an exemplary embodiment of the image mapper optics 121. Beamlets enter a first faceted prism array 802 as a rectilinear array 804. The first faceted prism array 802 convert the rectilinear array 804 into a linear array 806 and prism angles deflect the linear array toward a second faceted prism array 812. The second faceted prism array 812 makes all beams coplanar. The second faceted prism array 812 has prism angles that deflect beamlets such that all beamlets are passed to spectrometer.

Figure 9:
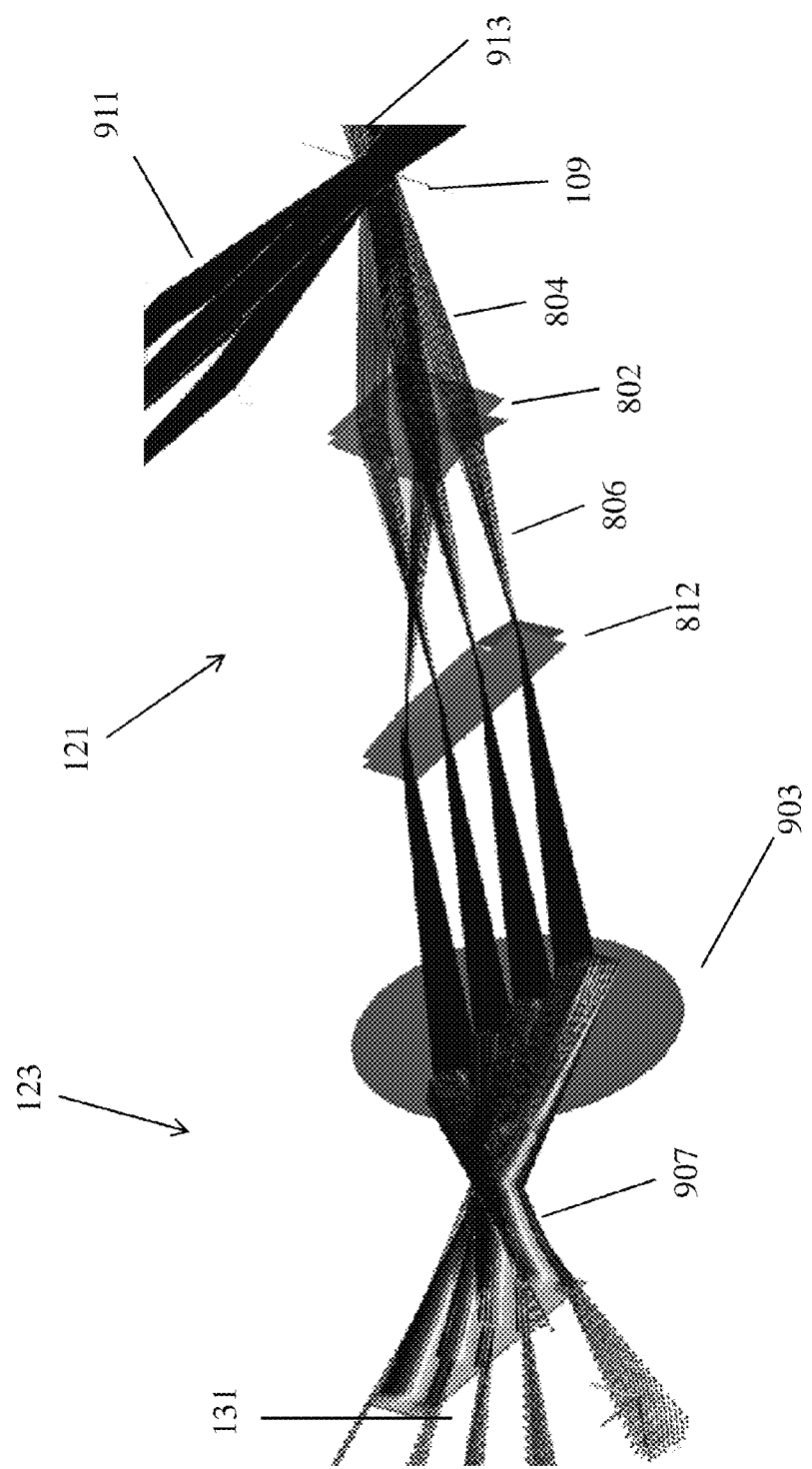
FIG. 9 is a diagram of the image mapper and spectrometer, according to certain embodiments.

FIG. 9 is a schematic representation of the image mapper 121 and spectrometer 123 according to certain embodiments. Light from the sample 911 and the reference minor 913 is recombined at the beam splitter 109 and projected to the image mapper 121. The image mapper 121 spatially separates the beamlets and converts them into a linear array. Beamlets enter a first faceted prism array 802 as a rectilinear array 804. The first faceted prism array 802 convert the rectilinear array 804 into a linear array 806 and prism angles deflect the linear array toward a second faceted prism array 812. The second faceted prism array 812 makes all beams coplanar. The second faceted prism array 812 has prism angles that deflect beamlets such that all beamlets are passed to spectrometer. In an exemplary embodiment, the spectrometer is comprised of a relay lens and a diffraction grating 903 which decompose the interferograms into their spectral components 907. The spectral components 907 of each interferogram are projected onto the focal plane array 131 which quantifies the photons. In some embodiments, the photodetector is a complementary metal oxide semiconductor (CMOS) area sensor. In still other embodiments the photodetector is a charge-coupled device (CCD).

Figure 10:
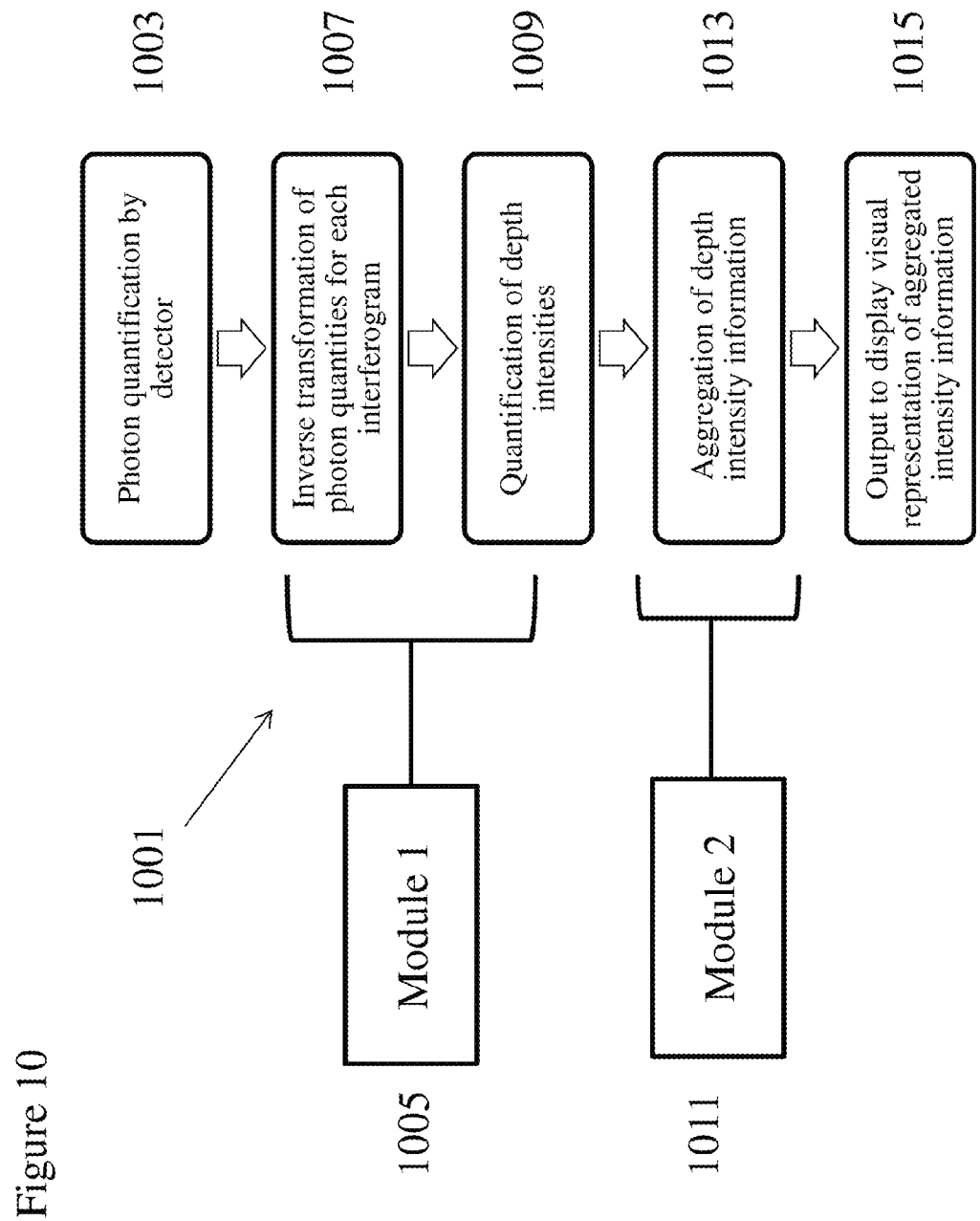
FIG. 10 is a block diagram of the image analysis process according to certain embodiments.

FIG. 10 is a block diagram of the image processing process 1001 according to certain embodiments. Data from the photodetector 803 is sent to a first computer module 1005. The first module 1005 performs an inverse transformation 1007 of the photon quantities for each interferogram to generate an image showing the intensity of the interference at each depth in the tissue for each beam. A second computer module 1011 receives input from the first computer module 1005 and receives said quantifications of depth intensities 1009. The second computer module 1011 aggregates depth intensity information 1013 for each beamlet interferogram and assembles a composite image of the sample being imaged. The aggregation of depth intensity information 1013 is then sent to a visual display 1015 for evaluation by the user.

In certain embodiments, the aggregates depth intensity information is used to quantify retinal nerve thinning. In further embodiments, the aggregate depth intensity information is used to quantify retinal thickening.

Figure 11:
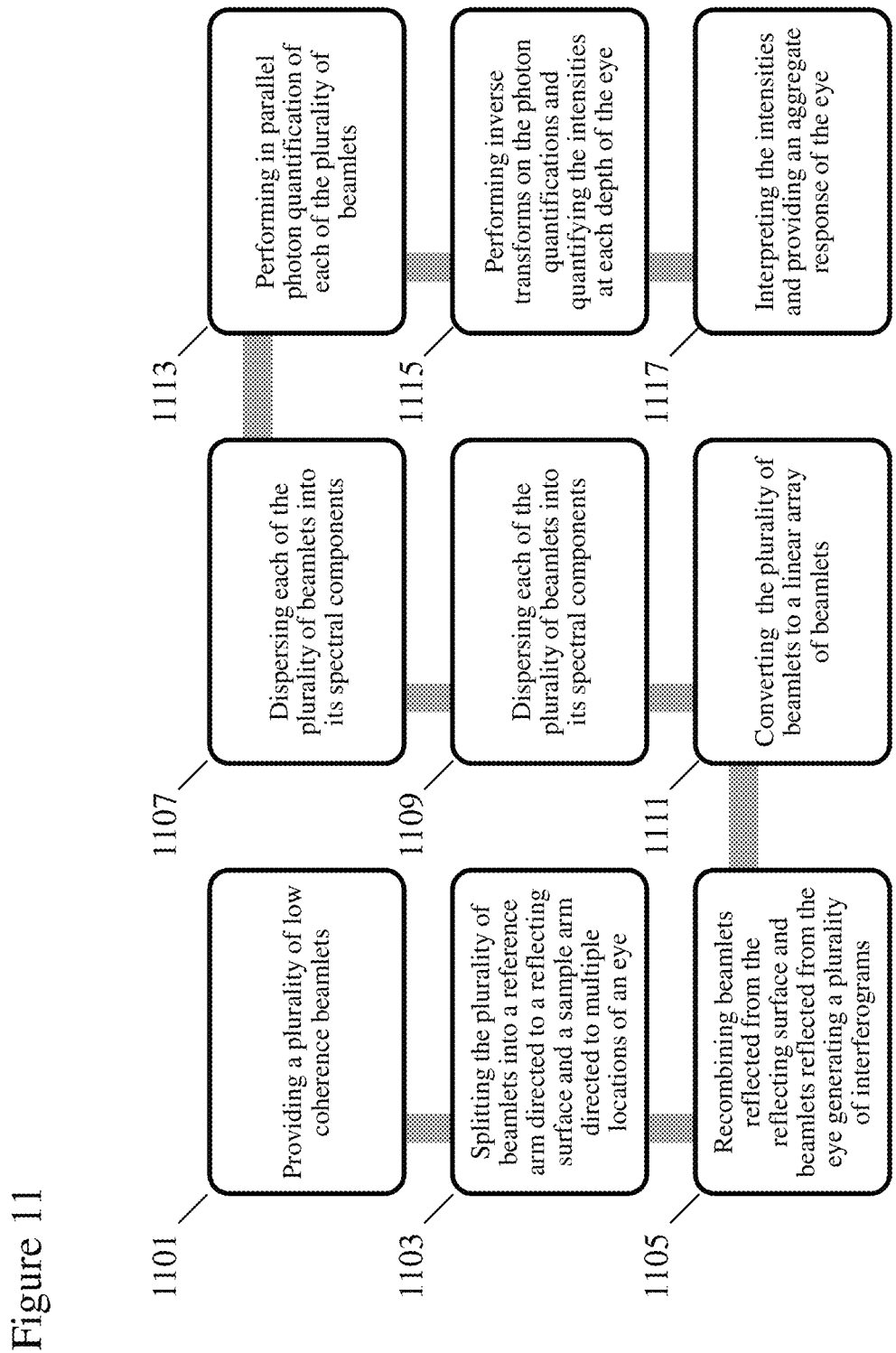
FIG. 11 is a flow chart of disclosed methods according to certain embodiments.

According to certain embodiments, as best shown in FIG. 11, provided is a method of imaging an eye that comprises providing a plurality of low coherence beamlets 1101, splitting the plurality of beamlets into a reference arm directed to a reflecting surface and a sample arm directed to multiple locations of an eye 1103, recombining beamlets reflected from the reflecting surface and beamlets reflected from the eye generating a plurality of interferograms 1105, converting the plurality of beamlets to a linear array of beamlets 1107; dispersing each of the plurality of beamlets into its spectral components 1109, performing in parallel photon quantification of each of the plurality of beamlets 1111.

According to certain alternative embodiments, provided is a method of imaging an eye that comprises providing light from a low coherence light source and splitting the light with a beam splitter into a reference arm and a sample arm. The method further comprises splitting the sample arm into a plurality of beamlets and directing the plurality of beamlets to the region of the eye to be imaged; transmitting the reference arm to a reflecting surface; recombining light reflected from the eye and the reflecting surface generating a plurality of interferograms; converting the plurality of beamlets to a linear array of beamlets; dispersing each of the plurality of beamlets into its spectral components; performing in parallel photon quantification of each of the plurality of beamlets.

In certain aspects, the method further comprising performing inverse transforms on the photon quantifications and quantifying the intensities at each depth of the eye 1113. In further aspects, the method further comprises interpreting the intensities and providing an aggregate response of the ocular tissues 1115. In still further aspects, the disclosed method further comprises calculating retinal thickening based on the aggregate response of ocular tissues 1117. In still further aspects, the method further comprises calculating nerve fiber layer thinning.

Figure 12:
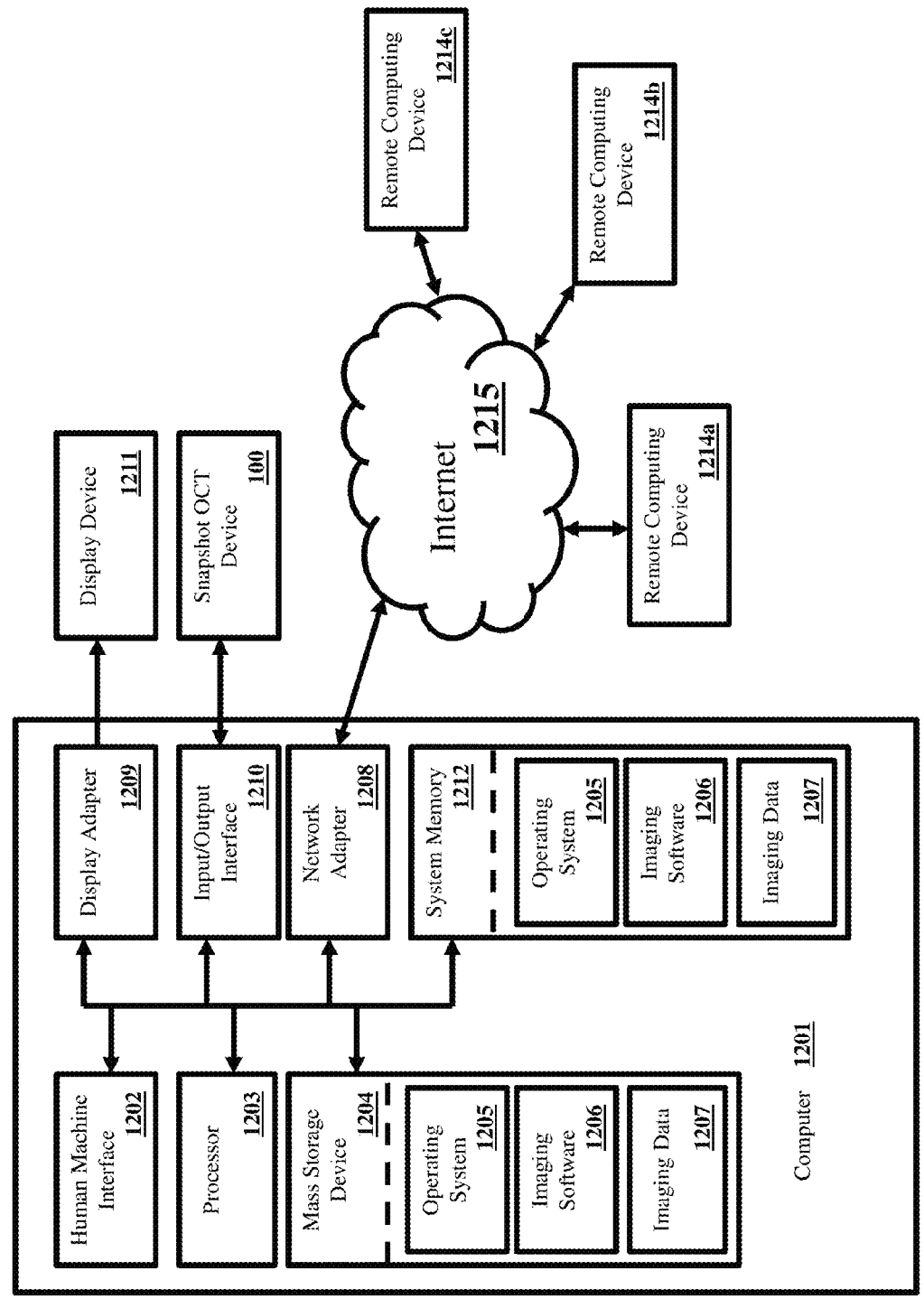
FIG. 12 shows a block diagram of an exemplary system.

FIG. 12 is a block diagram illustrating an exemplary operating environment for performing the disclosed method. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the system and method comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed system and method can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed method can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a computing device in the form of a computer 1201. The components of the computer 1201 can comprise, but are not limited to, one or more processors or processing units 1203, a system memory 1212, and a system bus 1213 that couples various system components including the processor 1203 to the system memory 1212. In the case of multiple processing units 1203, the system can utilize parallel computing.

The system bus 1213 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 1213, and all buses specified in this description can also be implemented over a wired or wireless network connection and each of the subsystems, including the processor 1203, a mass storage device 12012, an operating system 1205, imaging software 1206, imaging data 1207, a network adapter 1208, system memory 1212, an Input/Output Interface 1210, a display adapter 1209, a display device 1211, and a human machine interface 1202, can be contained within one or more remote computing devices 1214*a,b,c* at physically separate locations, connected through buses of this form, in effect implementing a fully distributed system.

The computer 1201 typically comprises a variety of computer readable media. Exemplary readable media can be any available media that is accessible by the computer 1201 and comprises, for example and not meant to be limiting, both volatile and non-volatile media, removable and non-removable media. The system memory 1212 comprises computer readable media in the form of volatile memory, such as random access memory (RAM), and/or non-volatile memory, such as read only memory (ROM). The system memory 1212 typically contains data such as imaging data 1207 and/or program modules such as operating system 1205 and imaging software 1206 that are immediately accessible to and/or are presently operated on by the processing unit 1203.

In another aspect, the computer 1201 can also comprise other removable/non-removable, volatile/non-volatile computer storage media. By way of example, FIG. 12 illustrates a mass storage device 12012 which can provide non-volatile storage of computer code, computer readable instructions, data structures, program modules, and other data for the computer 1201. For example and not meant to be limiting, a mass storage device 12012 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 12012, including by way of example, an operating system 1205 and imaging software 1206. Each of the operating system 1205 and imaging software 1206 (or some combination thereof) can comprise elements of the programming and the imaging software 1206. Imaging data 1207 can also be stored on the mass storage device 12012. Imaging data 1207 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 1201 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the processing unit 1203 via a human machine interface 1202 that is coupled to the system bus 1213, but can be connected by other interface and bus structures, such as a parallel port, game port, an IEEE 13912 Port (also known as a Firewire port), a serial port, or a universal serial bus (USB).

In yet another aspect, a display device 1211 can also be connected to the system bus 1213 via an interface, such as a display adapter 1209. It is contemplated that the computer 1201 can have more than one display adapter 1209 and the computer 1201 can have more than one display device 1211. For example, a display device can be a monitor, an LCD (Liquid Crystal Display), or a projector. In addition to the display device 1211, other output peripheral devices can comprise components such as speakers (not shown) and a printer (not shown) which can be connected to the computer 1201 via Input/Output Interface 1210. Any step and/or result of the methods can be output in any form to an output device. Such output can be any form of visual representation, including, but not limited to, textual, graphical, animation, audio, tactile, and the like. In an aspect, the snapshot OCT apparatus 101 can be coupled to computer 1201 via Input/Output Interface 1210. For example, snapshot OCT apparatus 100 can transfer images captured to the computer 1201 for analysis and storage.

The computer 1201 can operate in a networked environment using logical connections to one or more remote computing devices 1214*a,b,c*. By way of example, a remote computing device can be a personal computer, portable computer, a server, a router, a network computer, a peer device or other common network node, and so on. Logical connections between the computer 1201 and a remote computing device 1214*a,b,c* can be made via a local area network (LAN) and a general wide area network (WAN). Such network connections can be through a network adapter 1208. A network adapter 1208 can be implemented in both wired and wireless environments. Such networking environments are conventional and commonplace in offices, enterprise-wide computer networks, intranets, and the Internet 1215.

For purposes of illustration, application programs and other executable program components such as the operating system 1205 are illustrated herein as discrete blocks, although it is recognized that such programs and components reside at various times in different storage components of the computing device 1201, and are executed by the data processor(s) of the computer. An implementation of imaging software 1206 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any method or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

In an aspect, provided is a snapshot spectral domain optical coherence tomographer comprising: a light source providing a plurality of beamlets; a beam splitter, splitting the plurality of beamlets into a reference arm and a sample arm; a first optical system that projects the sample arm onto multiple locations of a sample; a second optical system for collection of a plurality of reflected sample beamlets; a third optical system projecting the reference arm to a reflecting surface and receiving a plurality of reflected reference beamlets; a parallel interferometer that provides a plurality of interferograms from each of the plurality of sample beamlets with each of the plurality of reference beamlets; an optical image mapper configured to spatially separate the plurality of interferograms; a spectrometer configured to disperse each of the interferograms into its respective spectral components and project the spectral components of each interferogram in parallel; and a photodetector configured to receive the spectral components of each interferogram and provide in parallel photon quantification.

In certain aspects, the light source is a an array of broadband low-coherence light sources. In further aspects, the light source is a single broadband low-coherence light source split into a plurality of beamlets by a lenslet array.

In an aspect, the optical image mapper converts the beamlets into a linear array of beamlets.

In further aspects, the spectrometer further comprises a diffraction grating. In still further aspects, the spectrometer further comprises a prism.

In an aspect, the sample arm beamlets are projected to the sample in focus and in phase.

In certain aspects, the photodetector is a CMOS sensor. In further aspects, the photodetector is a CCD sensor.

In an aspect, the first and second optical systems are a fundus camera. In further aspects, the first and second optical systems are an anterior segment camera or a cornea camera.

In an aspect, the apparatus further comprises: a computer module wherein said computer module performs inverse transforms on the photon quantifications and quantifies intensities at each depth. In certain aspects, the apparatus further comprises a second computer module that interprets the intensities and provides an aggregate response of the object. In still further aspects, the aggregate response from the second computer module quantifies nerve fiber layer thinning. In certain aspects the aggregate response from the second computer module quantifies the amount of retinal thickening.

In certain aspects, the sample is a biological tissue. In further aspects, the biological tissue is selected from a group consisting of retina, cornea, epithelium, nervous tissue, or endothelium.

In certain aspects, provided is method of imaging an eye comprising: providing a plurality of low coherence beamlets; transmitting the plurality of low coherence beamlets to a beam splitter, wherein the beam splitter splits the plurality of beamlets into a reference arm directed to a reflecting surface and a sample arm directed to multiple locations of an eye; recombining beamlets reflected from the reflecting surface and beamlets reflected from the eye generating a plurality of interferograms; converting the plurality of beamlets to a linear array of beamlets; dispersing each of the plurality of beamlets into its spectral components; and performing in parallel photon quantification of each of the plurality of beamlets.

In an aspect, the method further comprises performing inverse transforms on the photon quantifications and quantifying the intensities at each depth of the eye. In certain aspects, the method further comprises interpreting the intensities and providing an aggregate response of the eye. In still further aspects, the method further comprises calculating retinal thickening. In yet further aspects, the method further comprises calculating nerve fiber layer thinning.

In an aspect, provided is a snapshot spectral domain optical coherence tomographer comprising: a housing and a system of optical components disposed in the housing capable of parallel optical coherence imaging of a sample; a broadband low coherence light source providing light to a beam splitter wherein the beam splitter splits the light into a reference arm and a sample arm; a first optical element converting the sample arm into a plurality of beamlets and focusing the plurality of beamlets on the sample; a reflecting surface reflecting light from the reference arm, wherein the light reflected from the reflecting surface is recombined with the plurality of beamlets reflected from the sample producing a plurality of beamlet interferograms; an optical image mapper configured to receive and spatially separate the plurality of beamlet interferograms; a spectrometer configured to disperse each of the beamlet interferograms into its respective spectral components and project the spectral components of each interferogram in parallel; a photodetector configured to receive the spectral components of each beamlet interferogram and provide in parallel photon quantification; and a computer module wherein said computer module performs inverse transforms on the photon quantifications and quantifies intensities at each depth.

Various modifications to the implementations described in this disclosure may be readily apparent to those skilled in the art, and the generic principles defined herein may be applied to other implementations without departing from the spirit or scope of this disclosure. Thus, nothing in this specification is intended to imply that any feature, characteristic, or attribute of the disclosed systems and processes is essential.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described apparatus components and systems can generally be integrated together.

What is claimed is:

1. A snapshot spectral domain optical coherence tomographer comprising:
   a. a light source providing a plurality of beamlets;
   b. a beam splitter splitting the plurality of beamlets into a reference arm and a sample arm;
   c. a first optical system that projects the sample arm onto multiple locations of the sample;
   d. a second optical system for collection of a plurality of reflected sample beamlets;
   e. a third optical system projecting the reference arm onto a reflecting surface and receiving a plurality of reflected reference beamlets;
   f. a parallel interferometer that provides a plurality of interferograms from each of the plurality of sample beamlets with each of the plurality of reference beamlets;
   g. an optical image mapper configured to spatially separate the beamlets;

h. a spectrometer configured to disperse each of the interferograms into its respective spectral components and project the spectral components of each interferogram in parallel; and i. a photodetector configured to receive the spectral components of each interferogram and provide in parallel photon quantification.

2. The apparatus of claim 1, wherein the light source is a an array of broadband low-coherence light sources.

3. The apparatus of claim 1, wherein the light source is a single broadband low-coherence light source split into a plurality of beamlets by a lenslet array.

4. The apparatus of claim 1, wherein the optical image mapper converts the beamlets into a linear array of beamlets.

5. The apparatus of claim 1 wherein the spectrometer further comprises a diffraction grating.

6. The apparatus of claim 1 wherein the spectrometer further comprises a prism.

7. The apparatus of claim 1 wherein the sample arm beamlets are projected to the sample in focus and in phase.

8. The apparatus of claim 1 wherein the first and second optical systems are a fundus camera.

9. The apparatus of claim 1 wherein the first and second optical systems are an anterior segment camera.

10. The apparatus of claim 1 further comprising:
a computer module wherein said computer module performs inverse transforms on the photon quantifications and quantifies intensities at each depth.

11. The apparatus of claim 10 further comprising:
a second computer module that interprets the intensities and provides an aggregate response of the object.

12. The apparatus of claim 11 wherein the aggregate response from the second computer module quantifies nerve fiber layer thinning.

13. The apparatus of claim 11 wherein the aggregate response from the second computer module quantifies the amount of retinal thickening.

14. The apparatus of claim 1 wherein the sample is selected from a group consisting of retina, cornea, epithelium, nervous tissue, or endothelium.

15. A method of imaging an eye comprising:
a. providing a plurality of low coherence beamlets;
b. transmitting the plurality of low coherence beamlets to a beam splitter, wherein the beam splitter splits the plurality of beamlets into a reference arm directed to a reflecting surface and a sample arm directed to multiple locations of an eye;
c. recombining beamlets reflected from the reflecting surface and beamlets reflected from the eye generating a plurality of interferograms;
d. converting the plurality of beamlets to a linear array of beamlets;
e. dispersing each of the plurality of beamlets into its spectral components;
f. performing in parallel photon quantification of each of the plurality of beamlets.

16. The method of claim 15 further comprising performing inverse transforms on the photon quantifications and quantifying the intensities at each depth of the eye.

17. The method of claim 16 further comprising interpreting the intensities and providing an aggregate response of the eye.

18. The method of claim 17 further comprising calculating retinal thickening.

19. The method of claim 17 further comprising calculating nerve fiber layer thinning.

20. A snapshot spectral domain optical coherence tomographer comprising:
a. a broadband low coherence light source providing light to a beam splitter wherein the beam splitter splits the light into a reference arm and a sample arm;
b. a first optical element converting the sample arm into a plurality of beamlets and focusing the plurality of beamlets on the sample;
c. a reflecting surface reflecting light from the reference arm, wherein the light reflected from the reflecting surface is recombined with the plurality of beamlets reflected from the sample producing a plurality of beamlet interferograms;
d. an optical image mapper configured to receive and spatially separate the plurality of beamlet interferograms;
e. a spectrometer configured to disperse each of the beamlet interferograms into its respective spectral components and project the spectral components of each interferogram in parallel;
f. a photodetector configured to receive the spectral components of each beamlet interferogram and provide in parallel photon quantification; and
g. a computer module wherein said computer module performs inverse transforms on the photon quantifications and quantifies intensities at each depth.

* * * * *